United States Patent [19]

Marthaler

[11] Patent Number: 4,520,657
[45] Date of Patent: Jun. 4, 1985

[54] APPARATUS FOR DETERMINING THE PRESSURE OF CAPILLARY WATER, ESPECIALLY IN SOIL

[75] Inventor: Hans-Peter Marthaler, Adlikon bei Regensdorf, Switzerland

[73] Assignee: Dr. von Ballmoos AG, Horgen, Switzerland

[21] Appl. No.: 515,121

[22] Filed: Jul. 19, 1983

[51] Int. Cl.³ ............................................. G01N 19/10
[52] U.S. Cl. ............................................. 73/73; 73/38; 73/726
[58] Field of Search .................. 73/73, 38, 726, 756, 73/DIG. 4

[56] References Cited

U.S. PATENT DOCUMENTS

| 3,049,914 | 8/1962 | Richards | 73/73 |
| 3,930,413 | 1/1976 | Laird et al. | 73/756 |
| 4,361,047 | 11/1982 | McMullen et al. | 73/DIG. 4 |

FOREIGN PATENT DOCUMENTS

| 158349 | 4/1954 | Australia | 73/73 |
| 801735 | 9/1958 | United Kingdom | 73/756 |
| 0652475 | 3/1979 | U.S.S.R. | 73/73 |

*Primary Examiner*—Donald O. Woodiel
*Attorney, Agent, or Firm*—Werner W. Kleeman

[57] ABSTRACT

The apparatus for determining the pressure of capillary water in the ground, especially in soil, is of a two-part design and comprises a probe tube and a pressure measuring device. The pressure is measured by means of an elastically deformable membrane. For pneumatically coupling the pressure measuring device with the probe tube the latter is closed by a pierceable and self-sealing closure member. A hollow needle suitable for piercing the closure member is attached to the pressure measuring device. Either at or in the elastically deformable membrane there are arranged mechanical-electrical transducers which can be connected to an electric measuring and evaluation instrument for indicating the pressure which corresponds to the deformation of the membrane.

6 Claims, 4 Drawing Figures

APPARATUS FOR DETERMINING THE PRESSURE OF CAPILLARY WATER, ESPECIALLY IN SOIL

BACKGROUND OF THE INVENTION

The present invention relates to a new and improved apparatus for determining the pressure of capillary water in the ground, especially in soil.

In its more particular aspects the present invention relates to a new and improved apparatus for determining the pressure of capillary watering the ground, especially in soil, which contains a probe tube adapted to be partially inserted into the soil and which can be filled with a measuring liquid. The probe tube is closed at that one of its ends, which is intended to be inserted into the soil, with a porous plug which is permeable for the measuring liquid. The probe tube is provided at its other end with a removable closure member which is particularly suitable for filling of the measuring liquid. The apparatus also is provided with a pressure measuring device for measuring the pressure within the probe tube above the measuring liquid.

Under the expression capillary water as mentioned above and in the following disclosure there is to be understood the non-absorptively combined portion of the water which is adherent to the soil. Such water forms the living space for aquatic soil organisms and can be absorbed through the roots of plants growing in the soil. The knowledge of the pressure of the capillary water, therefore, among other things, provides important information about the living conditions of the plants, so that such measurements are conducted for the purpose of observing changes in the capillary water resources within limited regions as well as for investigating the amount and the direction of flow of capillary water within relatively large regions.

Usually, relatively simple pressure gauges are used for measuring the pressure of capillary water. In one practical design the pressure gauge consists of a probe tube intended to be inserted into the ground and having a lower end which is closed by a porous plug formed of ceramic material. At the region of the upper end of the probe tube there is arranged a pressure measuring device. Usually, the pressure measuring device is a simple mercury manometer including a manometer tube, the upper end of which communicates with the upper end of the probe tube and the lower end of which is immersed into a mercury-filled container. During use of such a pressure gauge the probe tube is immersed into the ground until the plug reaches a predetermined depth. Thereafter, the probe tube is filled with water and the feed opening is closed in an air-tight fashion by a closure member. Water will exit through the porous plug in such an amount that the weight of the water column in the probe tube is equal to the weight of the mercury drawn into the manometer tube. The height of the drawn-in mercury column then corresponds to the starting point for the measurement. Afterwards, the ground surrounding the plug will additionally draw water through the porous plug of the probe until the subpressure or negative pressure originating therefrom is in equilibrium with the pressure of the capillary water. Such negative pressure corresponds to a further rise of the mercury in the manometer tube, and thus, can be indicated in a simple way as the height of the mercury column above the preceding defined starting point.

The disadvantages of such a simple pressure gauge are believed to be quite obvious. The accuracy of reading the pressure can not be randomly enhanced to any desired extent due to the meniscus of the mercury column in the manometer tube and possibly also in the mercury container as well as due to the hardly unavoidable parallax error. Therefore, reading errors of at least 1 mm Hg have to be tolerated. Furthermore, for the measurement of capillary water pressure in limited as well as in wide or large regions there are usually used several hundred pressure gauges. For the manometers thereof a relatively large amount of mercury will be required which is unpleasant to handle and harmful to the environment. The two last-mentioned disadvantages are aggravated by the fact that for measuring the capillary water pressure, generally the pressure gauges are inserted into the ground for more than one year and the areas to be investigated are only slightly protected, or, not at all, against trespassers or intruders.

SUMMARY OF THE INVENTION

Therefore, with the foregoing in mind it is a primary object of the present invention to provide a new and improved apparatus for determining the pressure of capillary water in the ground, especially in soil, which enables a high accuracy of measurement to be obtained.

Another important object of the present invention aims at providing an apparatus for determining the pressure of capillary water, especially in soil, the application of which does not include the use of any materials which are harmful to health or environment.

Still a further significant object of the present invention is directed to a new and improved apparatus for determining the pressure of capillary water, especially in soil, which requires no maintenance and servicing even over long periods of use.

Now in order to implement these and still further objects of the invention, which will become more readily apparent as the description proceeds, the apparatus of the present development is manifested by the feature that, the pressure measuring device comprises an elastically deformable membrane.

When using the apparatus according to the invention there can not only be avoided the reading errors which had to be tolerated of necessity, but it will even be possible to enhance the reading accuracy to a degree higher than required for the usual statistical evaluation. Additionally, the apparatus according to the invention does not contain any liquid or gaseous material which renders the use thereof more difficult and, in particular, it does not contain any material which is harmful for the user or for the environment in which the apparatus is used.

In a preferred design of the apparatus according to the invention the elastically deformable membrane is arranged in a housing which is removably attached to the probe tube and which is subdivided by the membrane to form a measuring chamber and a reference chamber. The reference chamber comprises an unobstructed opening leading to the environmental atmosphere and the measuring chamber is connectable to the internal space of the probe tube.

This preferred design as described above has the additional advantage that only one pressure measuring device is required for a multitude of probes.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
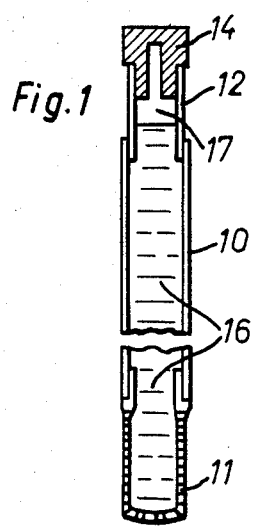
FIG. 1 is a schematic sectional view of a probe tube including a closure member of the apparatus according to the invention.

Describing now the drawings, it is to be understood that only enough of the construction of the apparatus for determining the pressure of capillary water, especially in soil, has been shown as needed for those skilled in the art to readily understand the underlying principles and concepts of the present development, while simplifying the showing of the drawings. Turning attention now specifically to FIG. 1, there has been schematically illustrated in section a probe tube 10 which has one end, which is the lower end in the drawing, which is intended to be inserted into the ground. At this lower tube end the probe tube 10 is closed by a porous ceramic plug 11. At the other opposite end, which is the upper end in the drawing, the probe tube 10 comprises a neck or neck portion 12 into which a removable closure member or plug 14 is intended to be introduced. During use of the apparatus the probe tube 10 is nearly completely filled with a suitable measuring liquid 16 which preferably is degassed water, so that an air cushion 17 remains between the surface 61 of the measuring liquid 16 and the bottom side of the closure member or plug 14.

Figure 2:
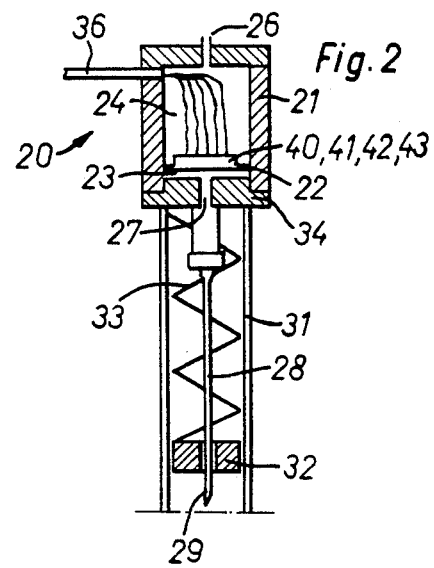
FIG. 2 is a schematic sectional view of the pressure measuring device including an elastically deformable membrane and a hollow needle of the apparatus according to the invention.

The pressure measuring device 20 which is intended for use with the probe tube 10 and which is shown in detail in FIG. 2 contains a housing 21, the internal space of which is subdivided into a relatively smaller measuring chamber 23 and a relatively larger reference chamber 24 by a membrane 22 which is deformable under the action of pressure. The reference chamber 24 is in direct flow communication with the external or ambient atmosphere by means of an opening 26 formed in one of the housing walls. The measuring chamber 23 is connected via a passage 27 to a hollow needle 28 which is arranged at the housing 21. The measuring chamber 24 communicates with the atmosphere present at the region of the tip 29 of the hollow needle 28 through the inner or internal passage thereof. The hollow needle 28 is encased by a guide tube 31 and is guided through the central bore of a contact or stop disk 32. The latter is displaceable from the open end of the guide tube 31 in the direction towards the bottom 34 of the housing 21 against the force of a spring 33.

The membrane 22 is formed of an elastically deformable material and coacts with a suitable mechanical-electrical transducer (not shown), the electrical properties of which change with the deformation of the membrane 22. Through a further opening in the reference chamber 24 there extends a cable 36 for connecting the transducer to a measuring and indicating instrument still to be described hereinbelow.

Figure 4:
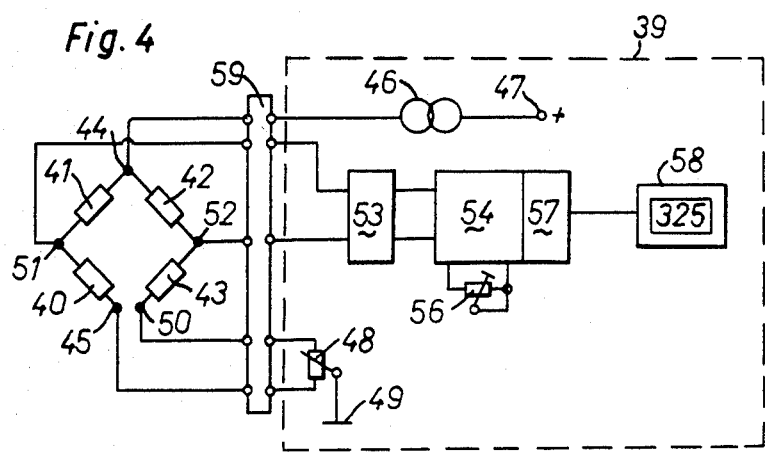
FIG. 4 is a block circuit of the electronic measuring and indicating instrument used with the apparatus according to the invention.

FIG. 4 shows a block circuit diagram of an electronic measuring and indicating instrument 39 to which the mechanical-electrical transducer 41-43 is connected. The transducer 41-43 contains four transducer elements 40, 41, 42 and 43 which are arranged along the circumference of the membrane 22 and symmetrically with respect to each other. These transducer elements 40, 41, 42, 43 are interconnected to form an open-type measuring bridge or bridge circuit. The terminal 44 of the measuring bridge is connected to a current source 46 which in turn is connected to a supply voltage source 47 of the apparatus. The oppositely situated "open" terminals 45 and 50 of the measuring bridge are connected to the ends of a potentiometer 48, the slider contact or tap of which leads to the apparatus ground 49. The two other terminals 51 and 52 of the measuring bridge are connected to the difference or differential input of an analog-digitial converter 54 via a filter 53. A potentiometer 56 is provided for the final balance and is operatively associated with the A/D converter 54. A coding circuit 57 is series connected to the output of the A/D converter 54 and the output signals of the coding circuit 57 are inputted to a suitable indicating device or indicator 58. The indicating device 58 preferably comprises an LCD-indicator with $3\frac{1}{2}$ digits.

The connecting lines leading from the transducer elements 40, 41, 42, 43 which form the measuring bridge, to the measuring and indicating instrument 39 lead through a plug-and-socket connection 59, one part or member of which is preferably mounted at the pressure measuring device 20. The plug-and-socket connection 59 enables the pressure measuring device 20 to be disconnected in a simple manner from the measuring and indicating instrument 39.

During use of the apparatus as described hereinbefore, the probe tube 10 is inserted into the ground to be investigated with the porous plug 11 in the leading position. The probe tube 10 is then filled with the measuring liquid 16 and closed by the closure member 14. Under the action of the weight of the liquid column formed by the measuring liquid 16 and the negative or subpressure of the capillary water in the soil, measuring liquid 16 then will egress through the porous plug 11 into the surrounding ground until the subatmospheric pressure or vacuum of the air cushion 17 compensates the pressure corresponding to the weight of the column of the measuring liquid 16 and the pressure of the capillary water. When the height 62 of the measuring liquid 16 in the probe tube 10 as measured above the center of the plug 11 (see FIG. 3) is known, the effective pressure of the capillary water can be very simply calculated from the negative pressure prevailing in the air cushion 17.

Figure 3:
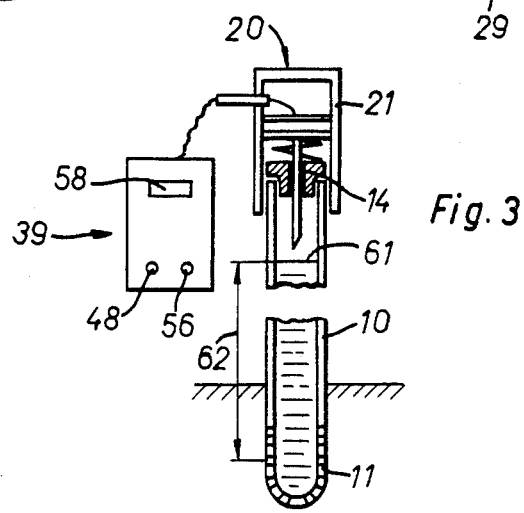
FIG. 3 is a schematic sectional view of the probe tube including the pressure measuring device attached to the top thereof in the apparatus according to the invention.

For measuring the negative or subpressure prevailing in the air cushion 17 the measuring bridge in the pressure measuring device 20 is connected to the measuring and indicating instrument 39 in an electrically conductive manner by means of the plug-and-socket connection 59. The branches of the measuring bridge are then balanced using the potentiometer 48 while the same pressures act on the two sides of the membrane 22, i.e., in the measuring chamber 23 and in the reference chamber 24. Finally, the pressure measuring device 20 is placed upon the top of the probe tube 10 and the hollow needle 29 is pierced through the closure member 14 as shown in FIG. 3. While the hollow needle 28 is piercing the closure member 14, the guide tube 31 is slipped onto the neck portion or neck 12 of the probe tube 10 and forms lateral guiding means. During this operation the contact or stop disk 32 compresses the spring 33 and thus limits the piercing depth of the hollow needle 28. Then a pressure balance or equilibrium will occur between the relatively large volume of the air cushion 17 present in the probe tube 10 and the relatively small measuring chamber 23 in the pressure measuring device 20. Subsequently, the membrane 22 and concomitantly therewith the transducer elements 40, 41, 42, 43 are deformed under the action of the pressure difference between the reference chamber 24 and the measuring chamber 23. The amount of deformation is proportional to the pressure difference. The deformation will change the voltage appearing at the terminals 51 and 52 of the measuring bridge, which voltage is delivered to the input of the A/D converter 54 via the filter 53. While the filter 53 does not affect this voltage it will prevent signals of higher frequencies, which may be caused by possible vibrations of the membrane 22, from reaching the A/D converter 54. In the A/D converter 54 the analog voltage change at the terminals 51, 52 of the measuring bridge is converted to a corresponding digital signal. In the series connected coding circuit or coder 57 the digital signals are coded to form a multiple number of activating or energization signals for the elements of the indicating device 58.

Preferably the closure member or stopper 14 for the probe tube 10 consists of nitrile rubber. It has been found that such material affords a pressure-tight closure of the probe tube 10 even for relatively extended periods of time, that such material tightly engages the hollow needle 28 when the same is pierced thereinto, and that the material tightly closes again when the hollow needle 28 is withdrawn, so that a number of, for example, up to thirty measurements can be conducted using the same closure member 14.

The membrane 22 simply may comprise a thin metal plate as used in barometers. Strain gauges can be used for the transducer elements. Piezo-resistive pressure pick-ups or transducers enable greater accuracy; such pressure pick-ups or transducers are commercially available in various designs. The individual parts or components of the measuring and indicating instrument 39 are also commercially available and, therefore, not described herein any further particular detail.

The measuring chamber 23 including the hollow needle 28 should have such a small volume that the pressure balance or equalization occurring upon introduction of the hollow needle 28 into the air cushion 17 only negligibly changes the pressure in the air cushion 17. The air cushion 17 in the probe tube 10 will have to be sufficiently large such that there is no direct pressure action on the measuring liquid 16 when the closure member 14 is pierced and such that the measuring liquid 16 can not be pressed out of the probe tube 10 through the plug 11.

It will be understood that the measuring and indicating instrument 39 can be constructed and adjusted in such a way that the error caused by the pressure balance or equalization occurring when the measuring chamber 23 is connected to the air cushion 17 is accounted for and that only the pressure of the capillary water is indicated at a known or constant height of the measuring liquid 16 in the probe tube 10. It will further be understood that the measuring and indicating instrument 39 can be adjusted or set for indicating the pressure in a usual or conventional unit for determining the pressure of the capillary water, such as cm WC(centimeter water column) or in any other measuring unit of pressure.

The apparatus according to the invention also may be used for measuring positive hydrostatic pressures.

In a tested practical embodiment of the apparatus according to the invention the sensitivity has been measured in the laboratory to be 0.3 bar per cubic centimeters. In a series of measurements taken in ground formed by sand and gravel the pressure of capillary water was found to be in the range of 150 to 900 cm WC; the average error for a total of 250 measurements amounted to only 3.75 cm WC.

While there are shown and described present preferred embodiments of the invention, it is to be distinctly understood that the invention is not limited thereto, but may be otherwise variously embodied and practiced within the scope of the following claims.
ACCORDINGLY,

What is claimed is:

1. An apparatus for determining the pressure of capillary water in the ground, especially in soil, said apparatus comprising:
    a probe tube adapted to be filled with a measuring liquid and to be partially inserted into the soil;
    said probe tube having a first end structured to be introduced into the soil to be investigated;
    a porous plug closing said first end of said probe tube and being permeable for said measuring liquid opposite said first end;
    said probe tube having a second end;
    a closure member closing said second end of said probe tube;
    a pressure measuring device for measuring the pressure prevailing in said probe tube above said measuring liquid;
    said pressure measuring device comprising an elastically deformable membrane;
    a hollow needle;
    said hollow needle being arranged to interconnect said measuring chamber and said internal space of said probe tube; and
    said closure member at said second end of said probe tube forming a plug of a pierceable and self-sealing material.

2. The apparatus as defined in claim 1, wherein:
said closure member is removable for filling said measuring liquid into said probe tube.

3. The apparatus as defined in claim 1, wherein:
said closure member is composed of nitrile rubber.

4. The apparatus as defined in claim 1, further including:
an electrical measuring and indicating instrument;
said elastically deformable membrane being structured as a piezo-electric transducer for generating electrical signals upon deformation thereof; and
said electrical signals being delivered to said electrical measuring and indicating instrument.

5. The apparatus as defined in claim 4, further including:
plug-and-socket connecting means for releasably interconnecting said piezo-electric transducer and said electric measuring and indicating instrument.

6. The apparatus as defined in claim 1, further including:

a guide tube for guiding said hollow needle;

said hollow needle being arranged in said guide tube;

a spring-loaded stop means provided in said guide tube and structured to form a disk;

said disk being provided with a central bore through which said hollow needle extends; and said disk being displaceable along said needle without hindrance.

* * * * *